United States Patent
Song et al.

(10) Patent No.: US 11,141,122 B2
(45) Date of Patent: Oct. 12, 2021

(54) METHODS AND DEVICES FOR PERFORMING THREE-DIMENSIONAL BLOOD VESSEL RECONSTRUCTION USING ANGIOGRAPHIC IMAGES

(71) Applicant: SHENZHEN KEYA MEDICAL TECHNOLOGY CORPORATION, Shenzhen (CN)

(72) Inventors: Qi Song, Seattle, WA (US); Youbing Yin, Kenmore, WA (US); Shubao Liu, College Park, MD (US); Xiaoxiao Liu, Bellevue, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 0 days.

(21) Appl. No.: 16/895,573

(22) Filed: Jun. 8, 2020

(65) Prior Publication Data

US 2020/0297300 A1    Sep. 24, 2020

Related U.S. Application Data

(63) Continuation of application No. 16/106,077, filed on Aug. 21, 2018, now Pat. No. 10,709,399.

(Continued)

(51) Int. Cl.
*A61B 6/00*    (2006.01)
*G06T 7/00*    (2017.01)
(Continued)

(52) U.S. Cl.
CPC .............. *A61B 6/504* (2013.01); *A61B 6/022* (2013.01); *A61B 6/466* (2013.01); *A61B 6/481* (2013.01);
(Continued)

(58) Field of Classification Search
CPC ... A61B 6/504; A61B 5/02007; A61B 6/5235; A61B 6/466; A61B 6/022;
(Continued)

(56) References Cited

U.S. PATENT DOCUMENTS 8,963,919 B2 *    2/2015    Mistretta ................ A61B 6/481
                                                                    345/424
9,375,191 B2 *    6/2016    Verstraelen ............ A61B 6/466
(Continued)

*Primary Examiner* — Allahyar Kasraian
(74) *Attorney, Agent, or Firm* — Bayes PLLC

(57) ABSTRACT

The disclosure provides a method and device for performing three-dimensional blood vessel reconstruction using projection images of a patient. The computer-implemented method includes receiving a first two-dimensional image of a blood vessel in a first projection direction and a three-dimensional model of the blood vessel. The method further includes determining, by a processor, a first optical path length at a selected position of the blood vessel based on the first two-dimensional image. The method also includes determining, by the processor, a second optical path length at the selected position of the blood vessel in the three-dimensional model. The method additional includes adjusting the three-dimensional model of the blood vessel, based on a comparison of the first optical path length and the second optical path length.

20 Claims, 11 Drawing Sheets

Related U.S. Application Data

(60) Provisional application No. 62/592,595, filed on Nov. 30, 2017.

(51) Int. Cl.
*A61B 6/02* (2006.01)
*G06T 7/11* (2017.01)

(52) U.S. Cl.
CPC .......... *A61B 6/5235* (2013.01); *G06T 7/0012* (2013.01); *G06T 7/11* (2017.01); *G06T 2207/30101* (2013.01); *G06T 2211/404* (2013.01)

(58) Field of Classification Search
CPC ..... A61B 2576/00; A61B 5/489; A61B 34/10; A61B 2034/2065; G06T 2207/30101; G06T 7/0012; G06T 2211/404; G06T 2200/04; G06T 7/11; G06T 17/00
See application file for complete search history.

(56) References Cited

U.S. PATENT DOCUMENTS

| | | |
|---|---|---|
| 9,811,939 B2 * | 11/2017 | Aben .................... A61B 8/5261 |
| 2005/0015006 A1 | 1/2005 | Mitschke et al. |
| 2006/0100528 A1 | 5/2006 | Chan et al. |
| 2007/0116342 A1 | 5/2007 | Zarkh et al. |
| 2011/0052035 A1 | 3/2011 | Kirchberg et al. |
| 2011/0135053 A1 | 6/2011 | Noordhoek et al. |
| 2019/0261937 A1 * | 8/2019 | Yoon ...................... A61B 6/466 |

* cited by examiner

METHODS AND DEVICES FOR PERFORMING THREE-DIMENSIONAL BLOOD VESSEL RECONSTRUCTION USING ANGIOGRAPHIC IMAGES

CROSS REFERENCE TO RELATED APPLICATION

The present application is a continuation of U.S. application Ser. No. 16/106,077, filed Aug. 21, 2018, which claims the benefits of priority to U.S. Provisional Application No. 62/592,595, filed Nov. 30, 2017. The contents of both applications are incorporated herein by reference in their entireties.

TECHNICAL FIELD

The present disclosure generally relates to image processing and analysis. More specifically, the present disclosure relates to a computer-implemented methods and devices for performing three-dimensional blood vessel reconstruction using angiographic images.

BACKGROUND

Rotational two-dimensional (2D) X-ray angiographic images provide valuable geometric information on vascular structures for diagnoses of various vascular diseases, such as coronary artery diseases and cerebral diseases. After a contrast agent (usually an x-ray opaque material, such as iodine) is injected into the vessel, the image contrast of the vessel regions is generally enhanced. Three-dimensional (3D) vascular tree reconstruction using the 2D projection images is often beneficial to reveal the true 3D measurements, including diameters, curvatures and lengths, of various vessel segments of interests, for further functional assessments of the targeted vascular regions.

Extant 3D reconstruction methods typically rely on 2D vessel structures segmented from multiple X-ray images from different imaging projection angles (such as a primary angle and a secondary angle). Usually, 2D vessel centerlines are first extracted from the segmented vessel regions, and 3D centerlines are then computed by establishing the proper projection imaging system geometry. One technical challenge presented by extant methods is the foreshortening issue. The vessel lengths are slightly different when viewed from different angles due to the nature of the projection imaging, causing foreshortening. Generally, foreshortening may be reduced by avoiding using images containing pronounced foreshortening vessel segments (represented with darker intensity) for 3D reconstruction. However, at least some level of foreshortening frequently occurs due to the curved geometrical nature of vessels and due to physiological motion of the patient during the imaging process (e.g., due to respiratory motion and cardiac motion).

Embodiments of the disclosure address the above problems by systems and methods for improved three-dimensional blood vessel reconstructions using angiographic images.

SUMMARY

Embodiments of the present disclosure include computer-implemented methods and devices for performing three-dimensional blood vessel reconstruction using projection images, which can be used independently or in combination with traditional three-dimensional reconstruction methods (e.g., epipolar geometry-based methods).

In one aspect, the disclosure is directed to a computer-implemented method for performing three-dimensional blood vessel reconstruction using projection images of a patient. The computer-implemented method includes receiving a first two-dimensional image of a blood vessel in a first projection direction and a three-dimensional model of the blood vessel. The method further includes determining, by a processor, a first optical path length at a selected position of the blood vessel based on the first two-dimensional image. The method also includes determining, by the processor, a second optical path length at the selected position of the blood vessel in the three-dimensional model. The method additional includes adjusting the three-dimensional model of the blood vessel, based on a comparison of the first optical path length and the second optical path length.

In another aspect, the disclosure is further directed to another computer-implemented method for performing three-dimensional blood vessel reconstruction using projection images of a patient. The computer-implemented method includes receiving a first two-dimensional image of a blood vessel in a first projection direction and a three-dimensional model of the blood vessel. The method further includes determining, by a processor, optical path lengths at a plurality of positions of the blood vessel in the three-dimensional model in the first projection direction. The method also includes determining, by the processor, a second two-dimensional image based on the determined optical path lengths at the plurality of positions. The method additionally includes adjusting the three-dimensional model of the blood vessel, based on a comparison of the first two-dimensional image and the second two-dimensional image.

In yet another aspect, the disclosure is also directed to a device for performing three-dimensional blood vessel reconstruction using projection images. The device includes an interface, which is configured to receive a first two-dimensional image of a blood vessel in a first projection direction and a three-dimensional model of the blood vessel. The device further includes a processor, which is configured to determine first optical path length at a selected position of the blood vessel based on the first two-dimensional image, determine a second optical path length at the selected position of the blood vessel in the three-dimensional model, and adjust the three-dimensional model of the blood vessel, based on a comparison of the first optical path length and the second optical path length.

Such a method and device may make full use of the intensity (e.g., grayscale) distribution pattern of the two-dimensional vessel (when filled with contrast agent) which is normally neglected and three-dimensional projection path information implied therein, effectively reducing the foreshortening phenomenon in the three-dimensional reconstruction, thereby improving the reconstruction accuracy of three-dimensional vascular tree. The scheme of the present disclosure assists the reconstruction of the three-dimensional image by considering the image pixel intensity information, and improves the reconstruction accuracy.

It is to be understood that both the foregoing general description and the following detailed description are exemplary and explanatory only and are not restrictive of the invention, as claimed.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments, and together with the description and claims, serve to explain the disclosed embodiments. When appropriate, the same reference numbers are used throughout the drawings to refer to the same or like parts. Such embodiments are demonstrative and not intended to be exhaustive or exclusive embodiments of the present method, device, or non-transitory computer readable medium having instructions thereon for implementing the method.

DETAILED DESCRIPTION

Reference will now be made in detail to the exemplary embodiments, examples of which are illustrated in the accompanying drawings. Wherever possible, the same reference numbers will be used throughout the drawings to refer to the same or like parts.

This description may use the phrases "in one embodiment," "in another embodiment," "in yet another embodiment," or "in other embodiments," all referring to one or more of the same or different embodiments in the present disclosure. Moreover, an element which appears in a singular form in the specific embodiments do not exclude that it may appear in a plurality (multiple) form. The technical term "optical path" used herein refers to the geometric path of rays propagating within a subject (not a vacuum). The technical term "optical path length" refers to the length of a geometric path along which the rays propagate in the subject. Consistent with the disclosure, "a length of the optical path in the blood vessel at a position in the first projection direction", refers to the length of the optical path along which the rays propagate in the first projection direction via this position within the blood vessel. The term "simulated optical path length" is intended to mean the length of the optical path obtained by simulation on the basis of a model.

Figure 1:
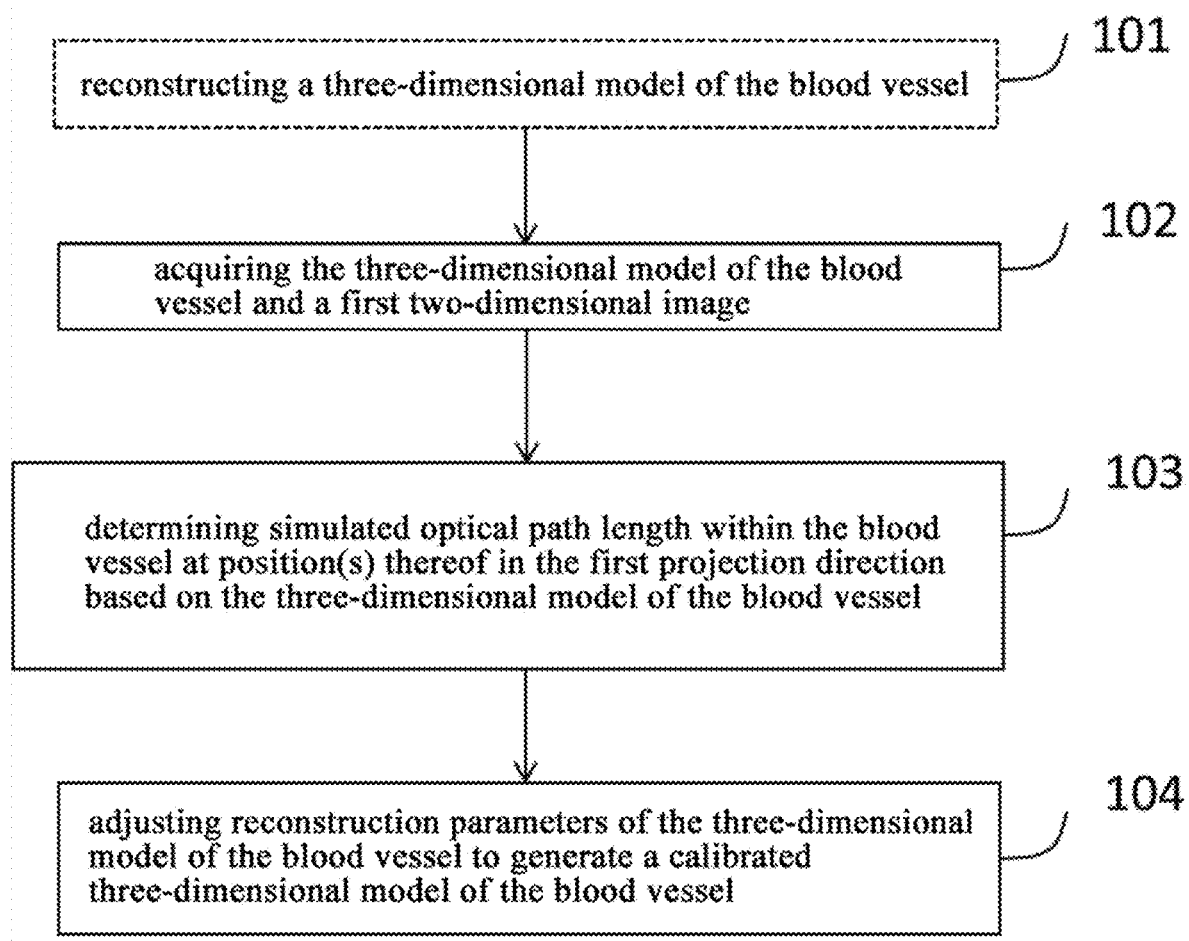
FIG. 1 shows a flowchart of an exemplary process for performing three-dimensional blood vessel reconstruction using X-ray angiographic images according to an embodiment of the present disclosure.

FIG. 1 shows a flowchart of an exemplary process 100 for performing three-dimensional blood vessel reconstruction using X-ray angiographic images according to an embodiment of the present disclosure. The process 100 begins with an acquiring step 102: acquiring a first two-dimensional image in the first projection direction of a blood vessel and a corresponding reconstructed three-dimensional model of the blood vessel. The three-dimensional model of blood vessel can be obtained using conventional three-dimensional model reconstruction techniques such as, but not limited to, epipolar geometry-based methods, stereotype reconstruction, or the like. For example, reconstruction of a three-dimensional model of a blood vessel may be performed based on at least two two-dimensional images respectively imaged from at least two different projection directions, so as to acquire the blood vessel three-dimensional model. The acquiring step 102 may also acquire an already reconstructed three-dimensional model of the blood vessel from a stereoscopic imaging device. In some embodiments, different from a simulated two-dimensional projection image obtained by projecting a three-dimensional model in a projection direction, the first two-dimensional image is a real two-dimensional image obtained by X-ray angiography of a blood vessel wherein transmitted X-rays are incident on a flat panel detector (CCD, CMOS, etc.). A pattern of the grayscale values in the two-dimensional image implies (encodes) three-dimensional projection path information.

In some embodiments, the first two-dimensional image may be a two-dimensional image based on which the blood vessel three-dimensional model is reconstructed. That is, when the two two-dimensional images as above are used to reconstruct a three-dimensional model of a blood vessel, any one of the two two-dimensional images may be used as the first two-dimensional image referred to in the present disclosure.

In other embodiments, the first two-dimensional image is a two-dimensional image captured by the imaging device, which is different from the two-dimensional image based on which the three-dimensional model of the blood vessel is reconstructed. For example, when the imaging device captures three two-dimensional images in the first projection direction, the second projection direction, and the third projection direction, respectively, two images respectively obtained in two directions (e.g., the first projection direction and the second projection direction) may be used to reconstruct a three-dimensional model of a blood vessel, and the other image (e.g. the third image) obtained in the other direction (e.g. the third projection direction) serves as the first two-dimensional image mentioned in present disclosure. In addition, for example, when the imaging device captures two two-dimensional images in the first projection direction and captures one two-dimensional image in the second projection direction, one of the two two-dimensional images in the first projection direction and the one two-dimensional image captured in the second projection direction may be used to reconstruct the three-dimensional model of the blood vessel, and the other two-dimensional image in the first projection direction may be used as the first two-dimensional image, so as to assist the reconstruction of the three-dimensional model of the blood vessel. In addition, for example, when the imaging device continuously captures a two-dimensional image in at least one or more projection directions, one image out of the obtained image sequences may serve as the first two-dimensional image.

In some embodiments, before the acquiring step 102, a three-dimensional model reconstructing step 101 may be optionally included. At the step 101, a three-dimensional model of the blood vessel may be reconstructed based on two or more two-dimensional images from different projection directions respectively.

After the acquisition step 102 is completed, a simulated optical path length determining step 103 is performed. At step 103, the simulated optical path length within the blood vessel at a position (i.e., at least one position) in the first projection direction may be determined based on the three-dimensional model of the blood vessel.

In one embodiment, the size at the position of the blood vessel in the first projection direction (a first X-ray transmission direction) in the three-dimensional model of the blood vessel may be determined as the simulated optical path length within the blood vessel at the corresponding position.

Figure 2:
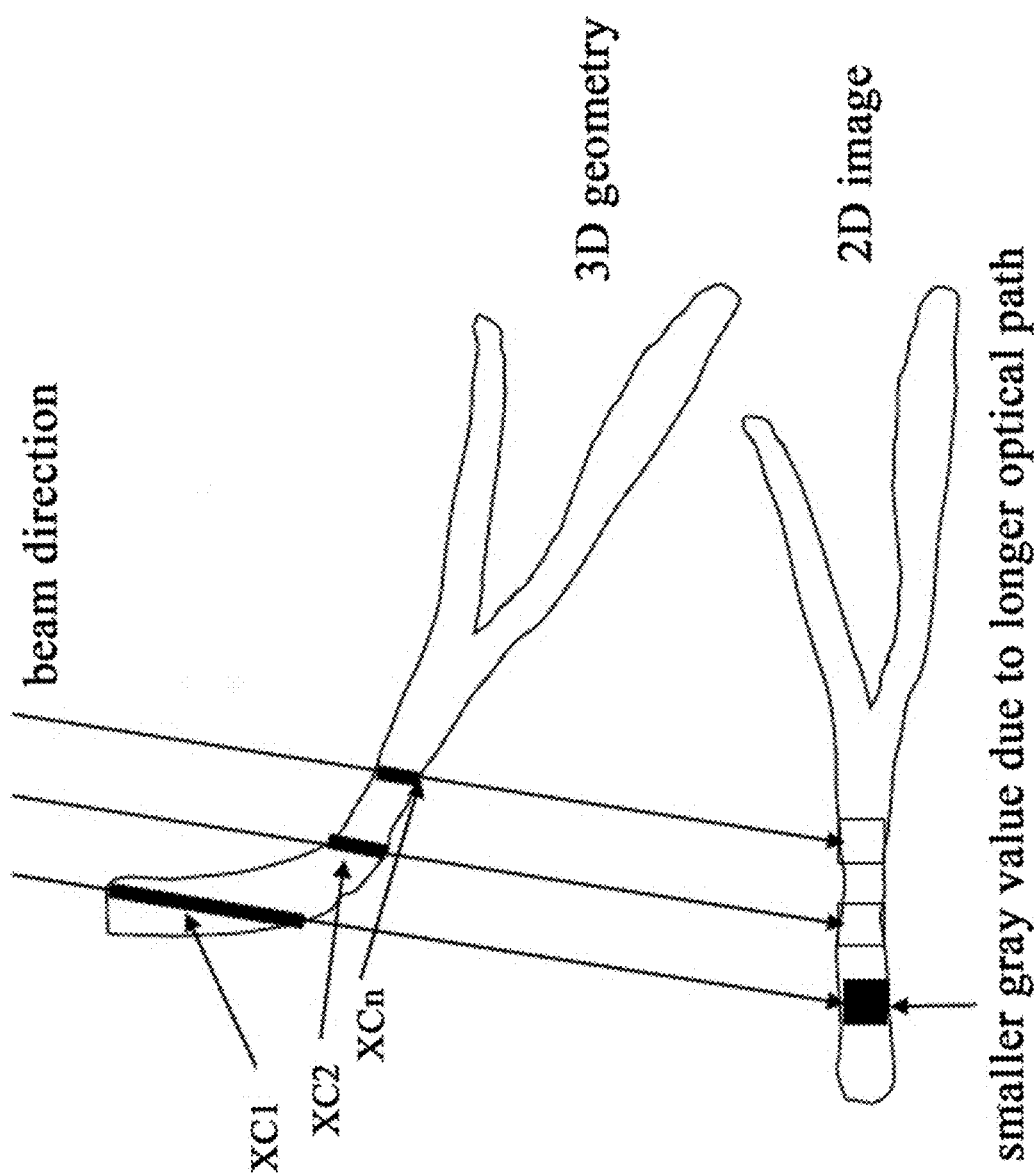
FIG. 2 schematically shows an illustration of optical path length within a blood vessel at several positions in a three-dimensional blood vessel model according to an embodiment of the present disclosure, and its relationship with a grayscale value of corresponding position in a two-dimensional image.

For example, as shown in FIG. 2, the sizes $x_{C1}$, $x_{C2}$, . . . , and $x_{Cn}$ at multiple positions of the blood vessel in the first projection direction in the three-dimensional model of the blood vessel (three-dimensional geometry) may be measured. Then each of the measured sizes may be used as the optical path length within the blood vessel at the corresponding position.

Figure 3:
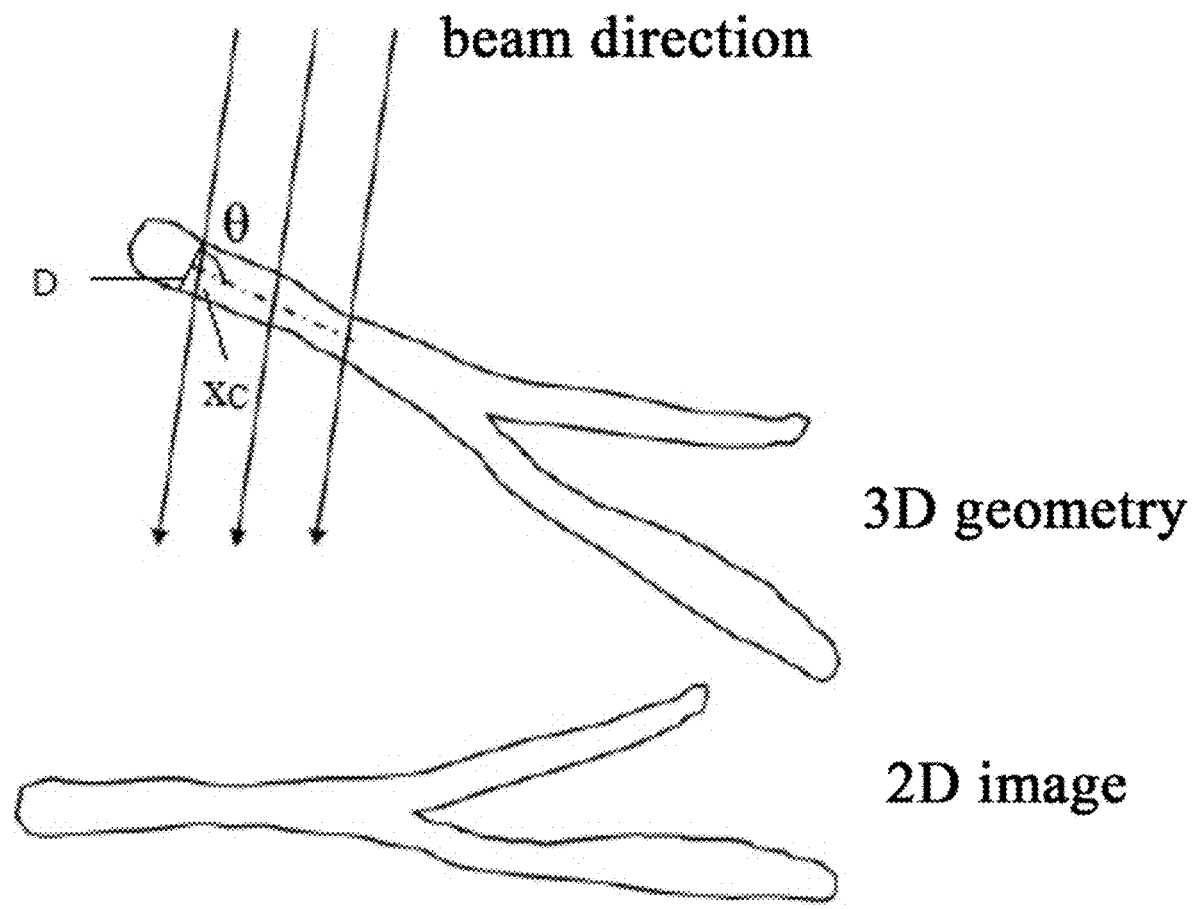
FIG. 3 illustrates a schematic diagram of a method of measuring an optical path length according to an embodiment of the present disclosure.

In another embodiment, the simulated optical path length $x_C$ may be obtained by radius estimation. As shown in FIG. 3, the direction pointed by the arrow is the first projection direction (beam direction). Firstly, the three-dimensional model of the blood vessel is projected in the first projection direction to obtain a second two-dimensional image (i.e. a simulated two-dimensional projection image) of the blood vessel three-dimensional model in the first projection direction. Then, according to the second two-dimensional image, the diameter D of a certain segment of the blood vessel is measured, and the angle θ between the center line of the segment of the blood vessel and the first projection direction is determined. Then, by using the following equation (1), the simulated optical path length $x_C$ of the segment of the blood vessel is calculated.

$$x_C = D/\sin\theta \quad\quad\quad \text{Equation (1)}$$

Then it proceeds to a three-dimensional reconstruction adjustment step 104. At the step 104, reconstruction parameters of the three-dimensional model of the blood vessel may be adjusted based on the simulated optical path length ($x_{C1}$, $x_{C2}$, . . . , and $x_{Cn}$) within the blood vessel at the position(s) in the first projection direction, intensity value at the corresponding position(s) of the blood vessel in the first two-dimensional image, and a relationship between intensity value at each position of a blood vessel in a second-dimensional image and an optical path length at the corresponding position. The adjusted reconstruction parameters may be utilized for three-dimension vessel reconstruction, so that a foreshortening of three-dimension vessel reconstruction may be rectified.

As shown in FIG. 2, when X-rays travel longer (i.e., the optical path is longer), there is more X-ray attenuation, and the intensity value of the transmitted beam is smaller, and accordingly, the grayscale value of the pixel is also smaller. Thus, embodiments of the present disclosure use grayscale values of the pixel to derive the optical path in the contrast agent (i.e., the optical path in the blood vessel) to infer the local vessel geometry.

Figure 4:
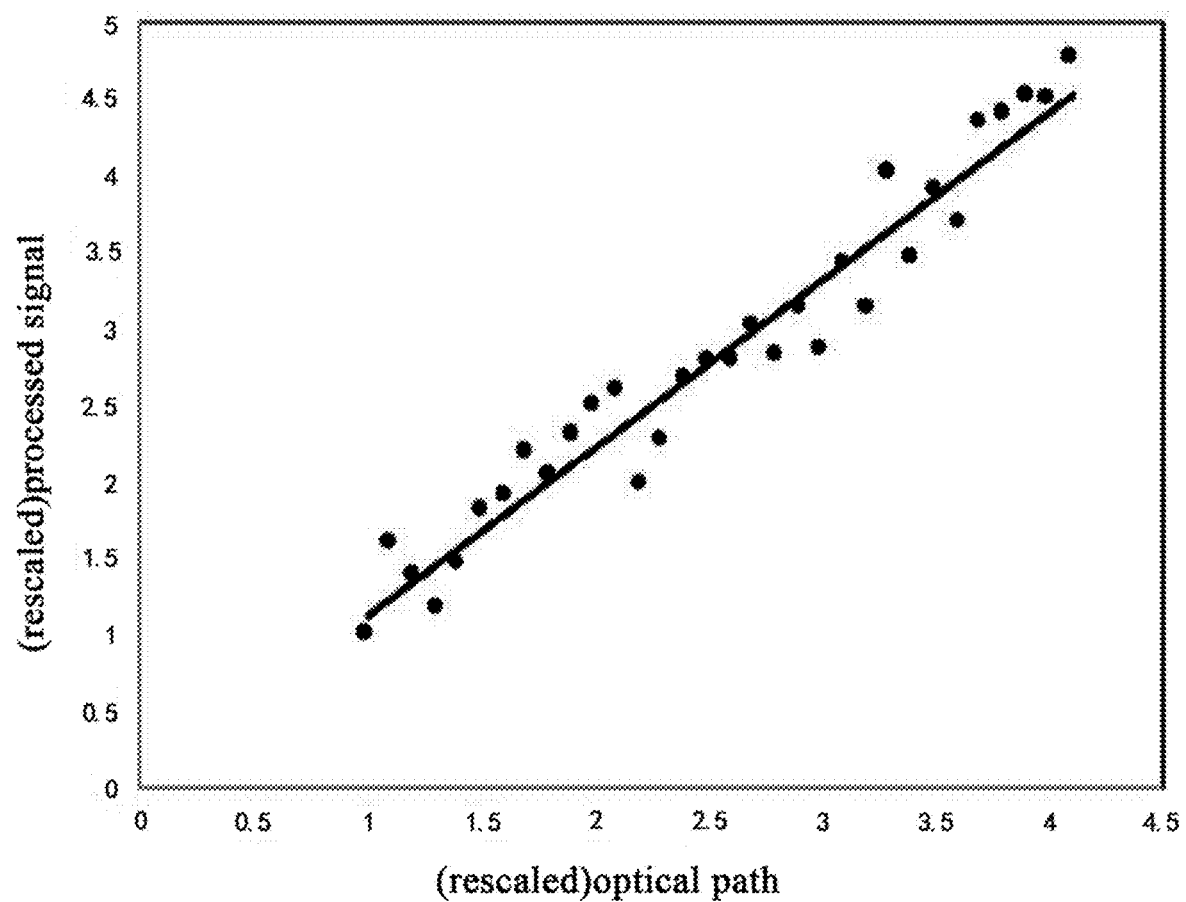
FIG. 4 shows a linear relationship between the value at each position of the blood vessel and the length of optical path at the corresponding position.

It is observed that there is an inherent relationship between the intensity value at each position of the blood vessel in the two-dimensional image and the optical path length at the corresponding position, under the same contrast agent injection condition for the same patient. When optical path length at each position of a blood vessel in a two-dimensional image are denoted by $x_C$, $\exp[x_C]$ has an inherent relationship with the intensity value, such as gray values $g_C$, at the corresponding position of the blood vessel in a two-dimensional image, such as an approximately linear relationship. The value obtained by removing background from the intensity value (such as the gray-scale value $g_C$) and logarithmically processing the intensity value at each position of the blood vessel, has a linear relationship with the optical path length $x_C$ at the corresponding position, as shown in FIG. 4.

The above-mentioned inherent relationship (for example, a linear relationship) can be explained through the following approximate derivation.

Specifically, the relationship between x-ray attenuation and optical path in the contrast agent may be defined by following Equation. (2).

$$\frac{I_T}{I_I} = \exp[-(\mu_C/\rho_C)x_C - (\mu_0/\rho_0)x_0] \quad\quad \text{Equation (2)}$$

where $I_I$ is the incident beam intensity, $I_T$ is the transmitted beam intensity, $\mu/\rho$ is the mass attenuation coefficient and x is the optical path. In addition, the subscripts c and o represent contrast agent and organ (i.e. vessel), respectively. In the absence of contrast agent, the x-ray beam absorption, due to the organ alone, is described by Equation (3).

$$\frac{I_B}{I_I} = \exp[-(\mu_0/\rho_0)x_0] \quad\quad \text{Equation (3)}$$

where $I_B$ is the transmitted beam intensity with only background.

By substituting Equation (3) into Equation (2), the relationship between the intensity of the light transmitted through the blood vessel at each position and the optical path length $x_C$ at the corresponding positions can be obtained, see Equation (4).

$$\frac{I_T}{I_B} = \exp[-(\mu_C/\rho_C)x_C] \quad\quad \text{Equation (4)}$$

The light transmitted the blood vessel at each position thereof may be incident onto a flat panel detector, so as to obtain a gray-scale two-dimensional image. Thereby, the intensity of the light transmitted through the blood vessel at each position is converted to intensity value (for example, gray value) at the corresponding position of the blood vessel in the two-dimensional image. It is verified that the conversion to gray-scale does not destroy the described inherent relationship, so that the inherent relationship between the intensity of the light transmitted through the blood vessel at each position and the optical path length $x_C$ at the corresponding position is maintained between the intensity value at each position of the blood vessel in the two-dimensional image and the optical path length $x_C$ at the corresponding position. Therefore, the reconstruction of the three-dimensional model can be guided by using the intensity values at the position(s) of the blood vessel in the two-dimensional images. Compared with the existing three-dimensional reconstruction technology that ignores the intensity value of two-dimensional images, the present disclosure considers the above relationship so that the reconstruction accuracy of the three-dimensional model can be improved. Hereinafter, in order to facilitate description, the transition between the intensity of the light transmitted through the blood vessel at the position(s) of and the intensity value at corresponding position(s) of the corresponding blood vessel in the two-dimensional image is ignored, and $I_T$ is used to denote the intensity value at position(s) of the blood vessel in the two-dimensional image, and $I_B$ is used to denote the background intensity at the corresponding position(s) of the blood vessel in the two-dimensional image.

In some embodiments, the reconstruction of the three-dimensional image may be assisted using the linear relationship between the processed intensity value at each position in the two-dimensional image and the optical path length $x_C$ at the corresponding position. By applying the logarithm to both sides of formula (4), the following Equation (5) can be obtained.

$$x_C = -\frac{\rho_C}{\mu_C}[\ln(I_T) - \ln(I_B)] \quad \text{Equation (5)}$$

It can be seen that the optical path length $x_C$ through the contrast agent is proportional to the processed image (i.e., that obtained by removing background from and logarithmically processing the image). That is, the value resulted by removing background and logarithmically processing the intensity value at each position of the blood vessel has a linear relationship with the optical path length $x_C$ at the corresponding position, as shown in FIG. 4.

In some embodiments, the value resulted by removing background from and logarithmically processing the intensity value at each position of the blood vessel in a two-dimensional image, i.e., $\ln(I_T)-\ln(I_B)$, may be obtained by the following steps: calculating the logarithm of the intensity value at each position of the blood vessel to obtain a first processed value $\ln(I_T)$; calculating the logarithm of background intensity value at each position of the blood vessel to obtain a second processed value $\ln(I_B)$; and subtracting the second processed value from the first processing value, so as to obtain the value resulted by removing background from and logarithmically processing the intensity value, $\ln(I_T)-\ln(I_B)$.

Figures 5A, 5B, 5C:
FIG. 5(a) illustrates a first two-dimensional image $I_T$.
FIG. 5(b) illustrates the estimated background image $I_B$.
FIG. 5(c) illustrates the first processed image $\ln(I_T)-\ln(I_B)$.

FIGS. 5(a) to 5(c) illustrate the image processing on how to obtain the value resulted by removing background from and logarithmically processing an intensity value at each position of a blood vessel in a two-dimensional image. FIG. 5(a) illustrates a first two-dimensional image $I_T$ (i.e. a measured X-ray angiographic image). FIG. 5(b) illustrates for example a background image $I_B$ estimated for the first two-dimensional image $I_T$ by utilizing image inpainting technology. And FIG. 5(c) illustrates the first processed image resulted by removing background and logarithmically processing, $\ln(I_T)-\ln(I_B)$. The methods of U.S. Provisional Application No. 62/591,437 (filed Nov. 28, 2017), which is incorporated herein by reference, may be used to process the images as above. In some embodiments, for example, background may be estimated by methods such as image inpainting. The log signal of the background-removed image has a linear correlation with optical paths.

In some embodiments, the relationship between the intensity value at each position of the blood vessel in a two-dimensional image and the optical path length at the corresponding position may be established in advance, in previous angiography and three-dimensional reconstruction of the same patient under the same contrast injection conditions, or the relationship is established in advance for part of the blood vessel in the same angiography and three-dimensional reconstruction. In some embodiments, in the same angiography and three-dimensional reconstruction, the foreshortening phenomenon may be avoided or decreased for the part of blood vessel, which is easy to achieve. And thus an accurate optical path length may be obtained by a reconstructed three-dimensional model based on the part of blood vessel, so that an accurate relationship between the intensity value at each position of the blood vessel in the two-dimensional image and the optical path lengths at the corresponding position may be established in advance. After the relationship is established in advance, the relationship can be recalled directly in a subsequent application scenario that satisfies the same contrast agent injection conditions.

When a three-dimensional model is reconstructed for a specific patient, difference in physiological characteristics (such as blood viscosity, respiratory motion, cardiac motion, etc.) and/or contrast agent parameters (such as injection time and injection volume) between previous and later angiographies may be small for him/her. Therefore, the relationship established in advance in the previous angiography and three-dimensional reconstruction or the relationship established in advance for the part of the blood vessel in the same angiography and three-dimensional reconstruction can be continuously adapted to the same patient. Compared to adopting the relationship obtained by means of the reconstruction of the three-dimensional model for other patients, it facilitates improving the accuracy of the reconstructed three-dimensional model of the blood vessel for the specific patient.

Figure 6:
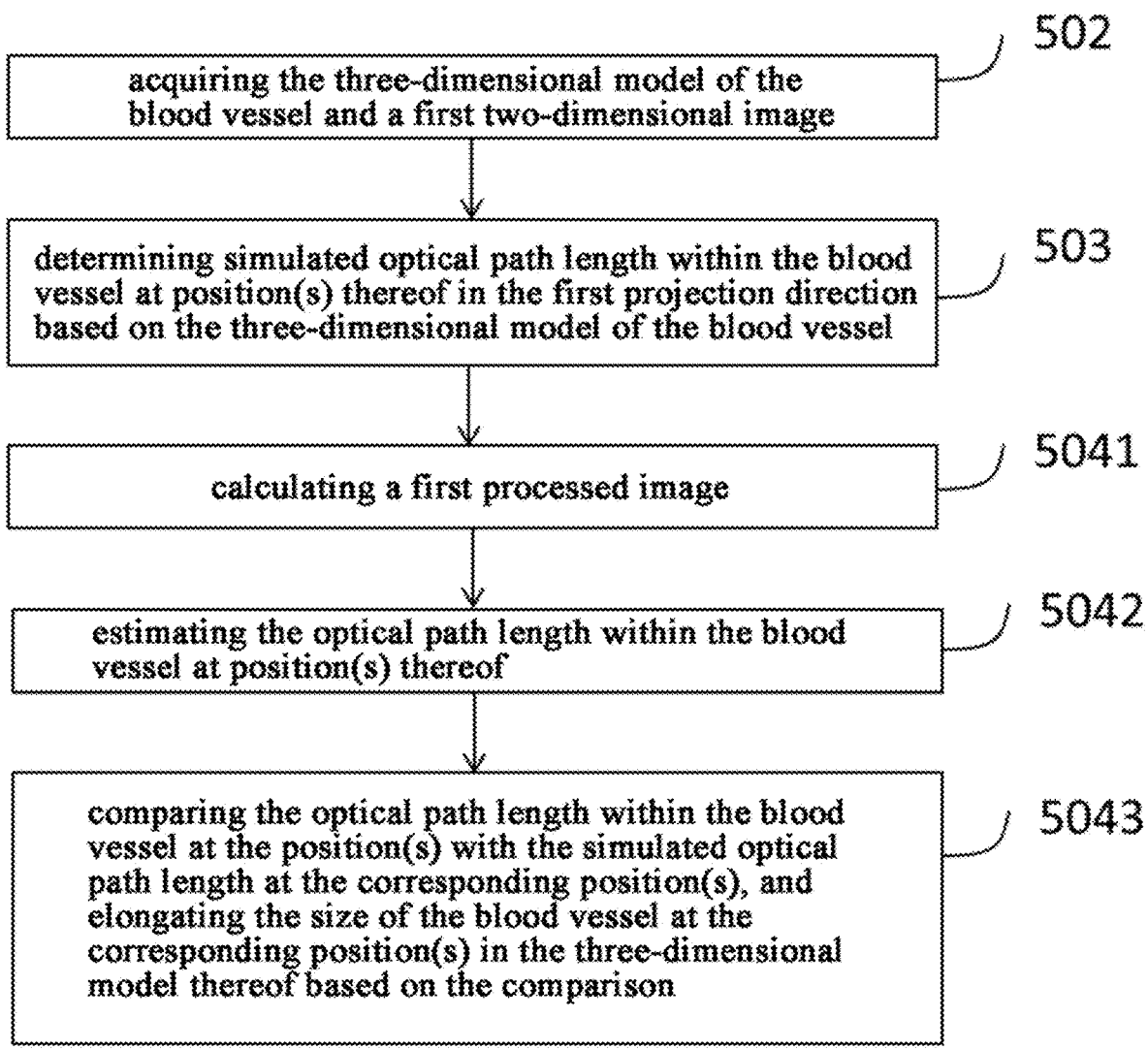
FIG. 6 depicts a flowchart of an exemplary process 500 for performing three-dimensional blood vessel reconstruction using X-ray angiographic images according to another embodiment of the present disclosure.
Figure 7:
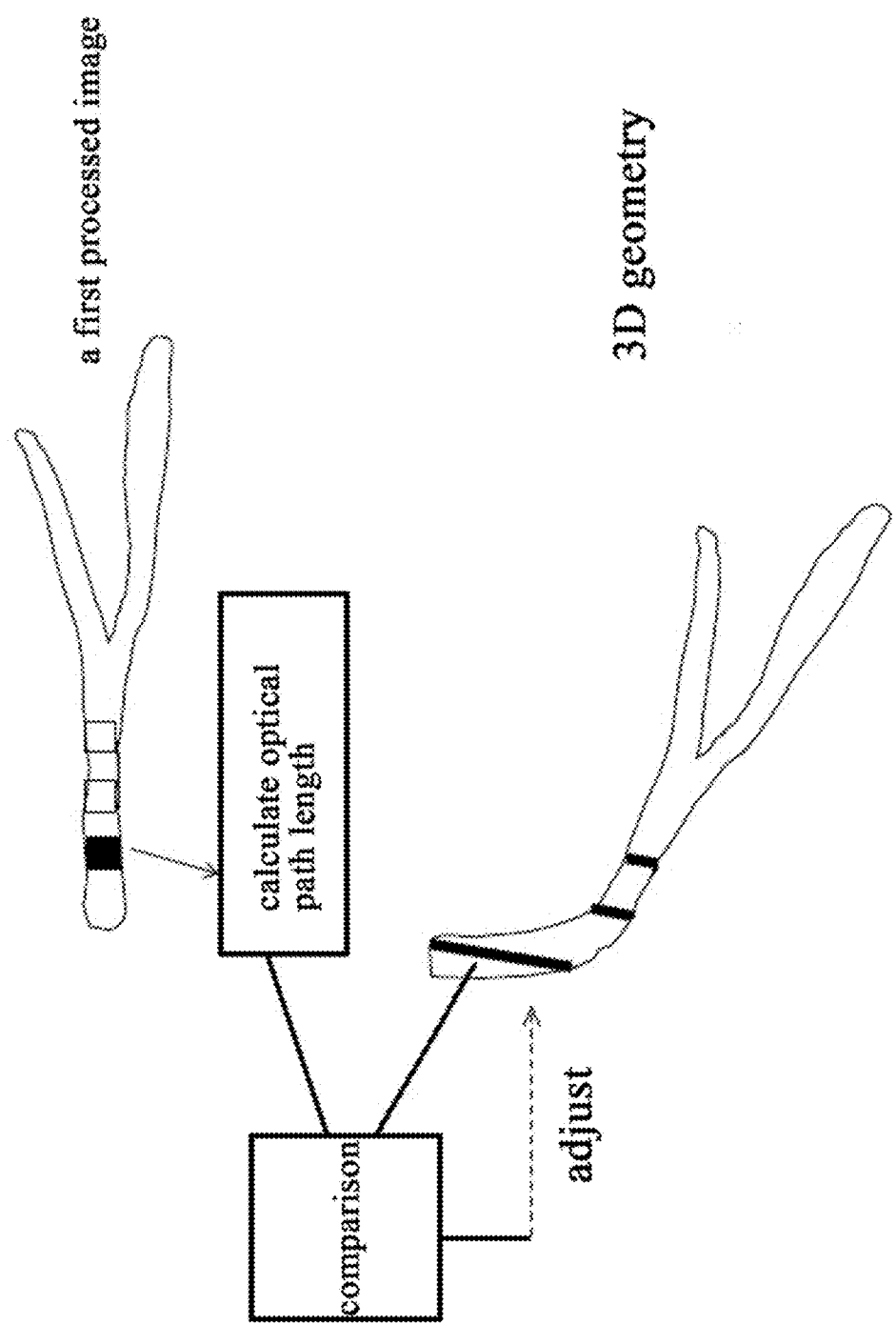
FIG. 7 is a schematic diagram showing a three-dimensional reconstruction adjustment step in the embodiment of FIG. 6.

In the following embodiment, as shown in FIG. 6, a flowchart of an exemplary process 500 for performing three-dimensional construction of a blood vessel using X-ray angiographic images according to another embodiment of the present disclosure is described. The exemplary process 500 includes the following steps. It begins with an acquisition step 502, wherein a reconstructed three-dimensional model of the blood vessel and a first two-dimensional image in the first projection direction corresponding thereto are acquired. Then, the process proceeds to a simulated light path length determining step 503. At step 503, the simulated optical path length within the blood vessel at position(s) in the first projection direction is determined based on the three-dimensional model of the blood vessel. After that, a three-dimensional reconstruction adjustment step is performed. With reference to both FIG. 6 and FIG. 7, the three-dimensional reconstruction adjustment step may include the following steps 5041~5043.

At step 5041, a first processed image resulted by removing background from and logarithmically processing the first two-dimensional image may be calculated. For example, in some embodiments, the step of calculating the first processed image may include (not illustrated in the drawings): calculating the logarithm of an intensity value of each pixel of the first two-dimensional image to obtain a third logarithmically processed image; then, inpainting intensity values of the blood vessel portion in the first two-dimensional image based on intensity values of the background pixels of the periphery of the blood vessel portion; calculating the logarithm of an intensity value of each pixel of the imprinted first two-dimensional image, so as to obtain a fourth logarithmically processed image; and then subtracting the fourth logarithmically processed image from the third logarithmically processed image, so as to obtain the first processed image, which is exemplified by FIG. 5(c).

At step 5042, the optical path length within the blood vessel at the position(s) may be estimated using the aforesaid linear relationship, which may be established in advance, based on the first processed image.

At step 5043, the optical path length within the blood vessel at the position(s) may be compared with the determined simulated optical path length within the vessel blood at the corresponding position(s), and the size of the blood vessel at the corresponding position(s) in the first projection direction in the three-dimensional model thereof may be elongated based on the comparison.

In one embodiment, the step 5043 may include: determining difference between the optical path length within the blood vessel at the position(s) and the simulated optical path length at the corresponding position(s) of the blood vessel; providing a warning if the difference is greater than a first predetermined threshold, otherwise, elongating the size of the blood vessel at the corresponding position(s) in the X-ray transmitting direction in the three-dimensional model of the blood vessel based on the difference, so as to eliminate the difference.

The first predetermined threshold may be a value preset empirically by a person skilled in the art, and this value is used to reflect the allowable degree of deviation of the reconstructed three-dimensional model. If the difference is greater than the first predetermined threshold, it means the deviation of the reconstructed three-dimensional model is relatively great, so a warning may be provided to draw the attention of a user (such as a surgeon or the like). Besides, if the difference is less than or equal to the first predetermined threshold, the size of the blood vessel at the corresponding position in the X-ray transmission direction in the three-dimensional model may directly modified (e.g. elongated) to eliminate the difference, thereby generating a calibrated blood vessel three-dimensional model.

Figure 8:
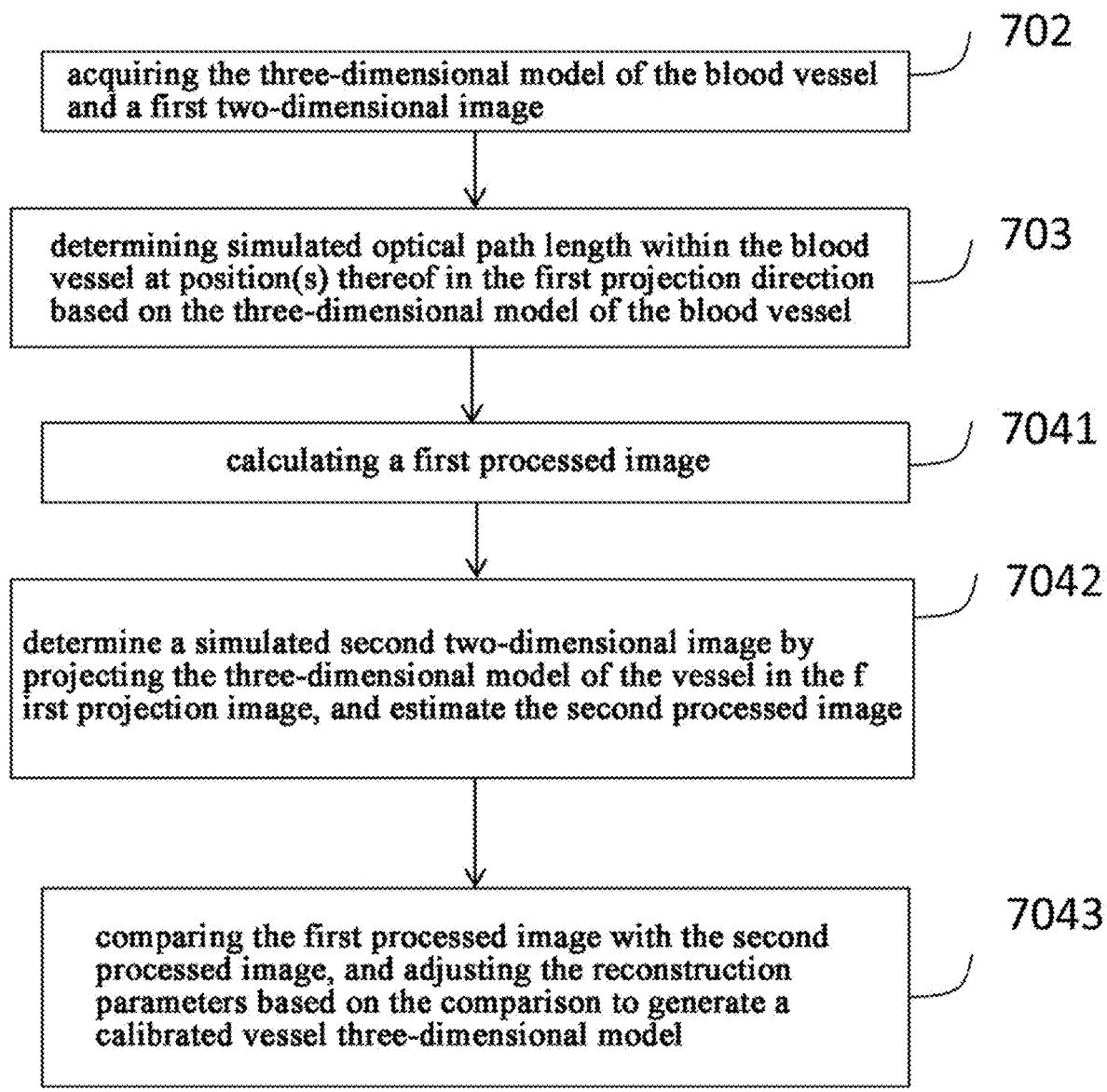
FIG. 8 depicts a flowchart of an exemplary process 700 for performing three-dimensional blood vessel reconstruction using X-ray angiographic images according to yet another embodiment of the present disclosure.

In the following embodiment, as shown in FIG. 8, a flowchart of an exemplary process 700 for performing three-dimensional blood vessel reconstruction using X-ray angiography images according to yet another embodiment of the present disclosure is described. The exemplary process 700 includes the following steps.

It begins with an acquisition step 702. At step 702, a reconstructed three-dimensional model of a blood vessel and a first two-dimensional image in the first projection direction corresponding thereto may be acquired.

Then, a simulated light path length determining step 703 is performed. At step 703, simulated optical path length within the blood vessel at position(s) in the first projection direction may be determined based on the three-dimensional model of the blood vessel.

Figure 9:
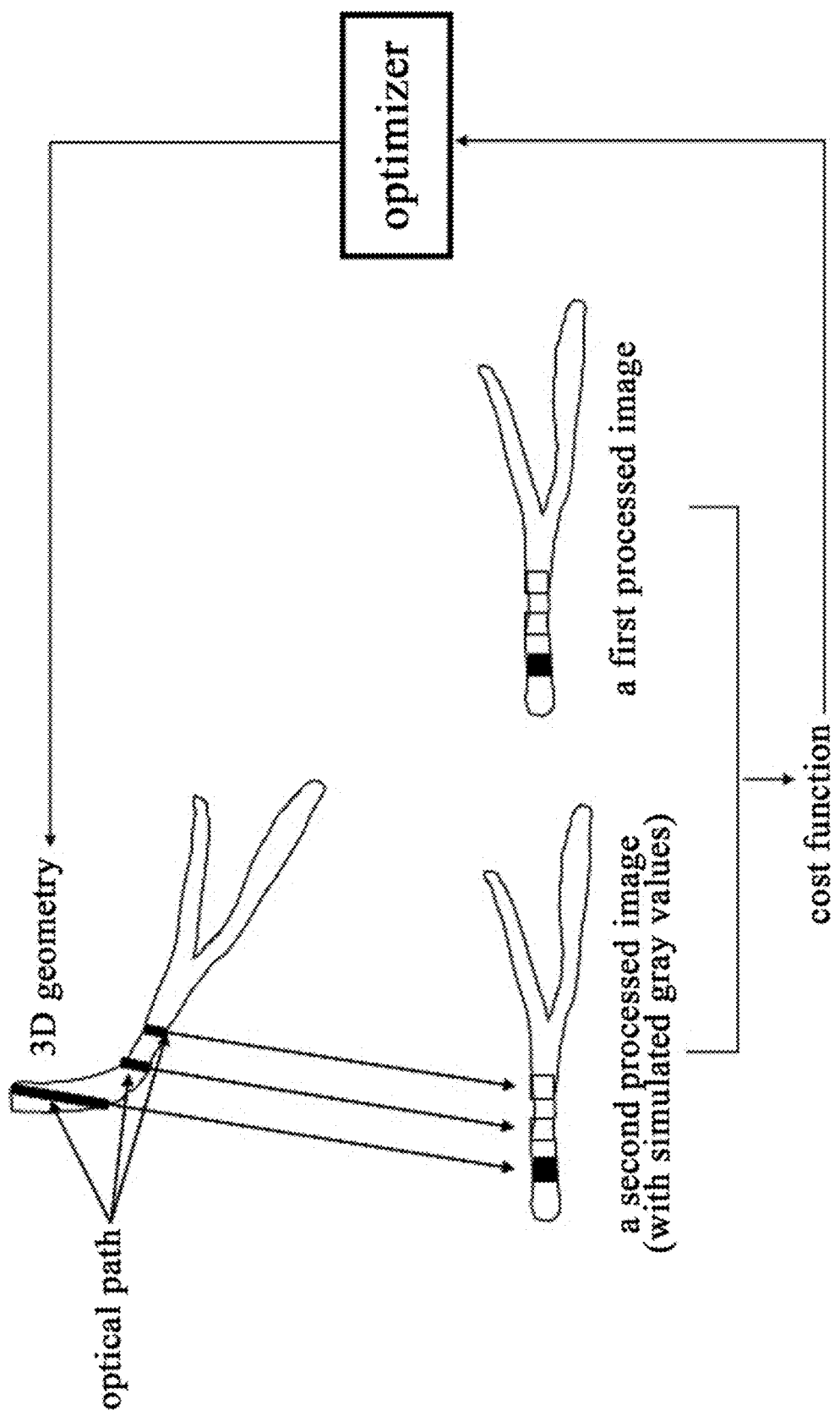
FIG. 9 is a schematic diagram showing a three-dimensional reconstruction adjustment step in the embodiment of FIG. 8.

After that, a three-dimensional reconstruction adjustment step is performed. With reference to FIG. 8 and FIG. 9, the three-dimensional reconstruction adjustment step includes the following steps 7041~7043. At step 7041, a first processed image resulted by removing background from and logarithmically processing the first two-dimensional image may be calculated. The process of calculating the first processed image may be performed as in the exemplary process 500.

At step 7042, the second processed image resulted by removing the background from and logarithmically processing a second two-dimensional image may be estimated using the linear relationship based on the determined simulated optical path length, wherein the second two-dimensional image is obtained by projecting the three-dimensional model of the blood vessel in the first projection direction. That is, according to the simulated optical path length and the linear relationship, processed (including background removing and logarithmically processing) intensity values may be obtained for corresponding position of the blood vessel (more specifically, each pixel point of the blood vessel region).

At step 7043, the first processed image may be compared with the second processed image, and the reconstruction parameters of the three-dimensional model of the blood vessel may be adjusted based on the comparison. The adjusted reconstruction parameters may be used to perform three-dimensional blood vessel reconstruction using the X-ray angiographic images.

Specifically, the pixel value (i.e., the processed intensity value) at each pixel position of the first processed image may be compared with the processed intensity value at the corresponding pixel position of the second processed image, and the reconstruction parameters of the three-dimensional model of the blood vessel may be adjusted based on the comparison. And three-dimensional vessel model reconstruction may be performed using the adjusted reconstruction parameters.

In some embodiments, the cost function is set as the difference obtained by the above comparison, and the reconstruction parameters of the three-dimensional model of the blood vessel may be adjusted by minimizing the cost function.

In other embodiments, with the cost function defined as the above difference, steps of the three-dimensional vessel reconstruction and reconstruction parameters may be performed iteratively, the cost function may be calculated and fed into an optimizer to update the reconstruction parameters and the corresponding three-dimensional blood vessel tree geometry (i.e., generating a calibrated three-dimensional model of a blood vessel). For example, the reconstruction parameters can be gradually updated using a Newton iteration method or the like until optimized reconstruction parameters are obtained. The optimized reconstruction parameters may be used to reconstruct an accurate three-dimensional model of the blood vessel.

In still other embodiments, step 7043 may include: determining a difference between the first processed image and the second processed image; providing a warning if the difference is greater than a second predetermined threshold, otherwise, adjusting the reconstruction parameters of the three-dimensional model of the blood vessel based on the comparison, so as to eliminate the difference.

The second predetermined threshold may be a value preset empirically by a person skilled in the art, which reflects the allowable degree of deviation of the reconstructed three-dimensional model. If the difference is greater than the second predetermined threshold, the deviation of the reconstructed three-dimensional model is considered as relatively great, so a warning is provided to draw the attention of the user (such as a surgeon or the like), and if the difference is less than or equal to the second predetermined threshold, the reconstruction parameters of the three-dimensional model of the blood vessel may be directly adjusted, thus adjusting the corresponding three-dimensional geometry of the vessel tree.

Figure 10:
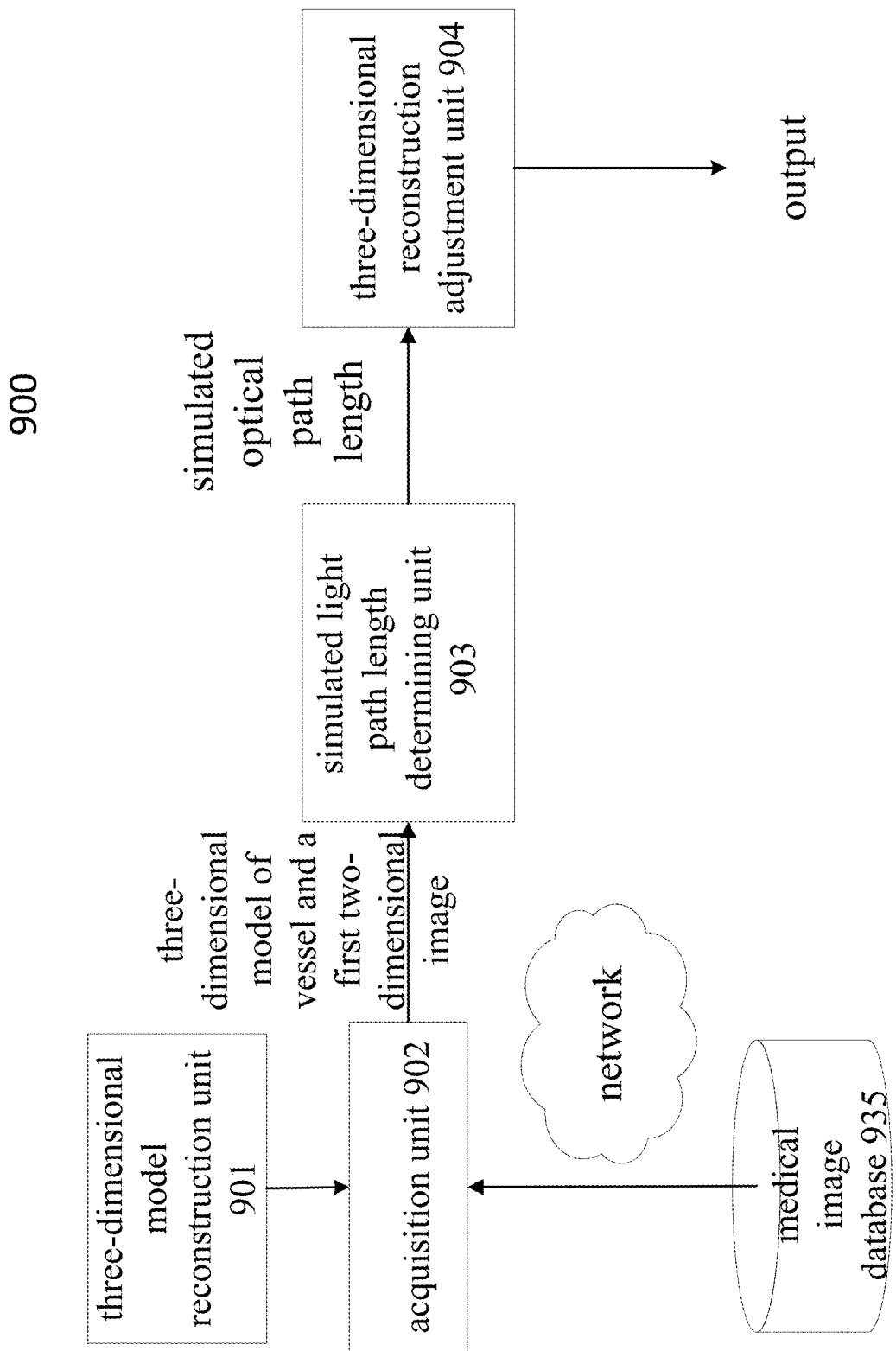
FIG. 10 illustrates a block diagram of a device 900 for performing three-dimensional blood vessel reconstruction using X-ray angiographic images.

FIG. 10 illustrates a block diagram of a device 900 for performing three-dimensional blood vessel reconstruction using X-ray angiographic images. The device 900 comprises: an acquisition unit 902, which is configured to acquire a first two-dimensional image in the first projection direction and a corresponding reconstructed three-dimensional model of the blood vessel; a simulated light path length determining unit 903, which is configured to determine simulated optical path length within the blood vessel at position(s) of the blood vessel in the first projection direction based on the three-dimensional model of the blood vessel; and a three-dimensional reconstruction adjustment unit 904, which is configured to adjust reconstruction parameters of the three-dimensional model of the blood vessel, based on the simulated optical path length within the blood vessel at the position(s) in the first projection direction, intensity values at the corresponding position(s) of the blood vessel on the first two-dimensional image, and a relationship between intensity value at each position of a blood vessel in a second-dimensional image and the optical path length at the corresponding position. The adjusted reconstruction parameters of the three-dimensional model of the blood vessel may be adopted to perform three-dimensional blood vessel reconstruction with X-ray angiographic images.

In some embodiments, the acquisition unit 902 may acquire a vascular medical image from the medical image database 935. The acquired vascular medical image may include a three-dimensional model of the blood vessel and/or a first two-dimensional image in the first projection direction corresponding to the three-dimensional model of the blood vessel. In some other embodiments, the acquiring unit 902 can directly acquire the three-dimensional model of a blood vessel and/or a first two-dimensional image corresponding to the three-dimensional model of the blood vessel in the first projection direction from an external device such as a medical image acquisition device (not shown). In still other embodiments, the acquisition unit 902 may acquire the above model and/or image from an image data storage device (not shown). In a modified embodiment, the acquisition unit 902 can acquire the required models and images from at least two of the above sources.

In one embodiment, device 900 may further include a three-dimensional model reconstruction unit 901. The three-dimensional model reconstruction unit 901 is configured to generate a reconstructed blood vessel three-dimensional model based on two or more two-dimensional images (the first two-dimensional image in the first projection direction may be included) respectively from different projection directions. The three-dimensional model reconstruction unit 901 may be connected to any one of the medical image database 935, the image acquisition device, and the image data storage device, so as to acquire the two-dimensional image(s) based on which the reconstruction is performed. The acquisition unit 902 may acquire the reconstructed three-dimensional model of a blood vessel from the three-dimensional model reconstructing unit 901. In one embodiment, the acquisition unit 902 may also acquire, from the three-dimensional model reconstructing unit 901, at least one image of the two-dimensional images, based on which the blood vessel three-dimensional model is reconstructed, and the device 900 may use the at least one image as the first two-dimensional image.

The acquisition unit 902 transmits the acquired three-dimensional model of the blood vessel and the corresponding first two-dimensional image in the first projection direction to the simulated optical path length determining unit 903. The simulated optical path length determination unit 903 transmits the determined simulation optical path length to the three-dimensional reconstruction adjustment unit 904, so that it may adjust reconstruction parameters of the three-dimensional model of the blood vessel, based on the simulated optical path length within the blood vessel at position(s) thereof in the first projection direction, intensity value at the corresponding position(s) of the blood vessel on the first two-dimensional image, and a relationship between intensity value at each position of a blood vessel in a second-dimensional image and optical path length at the corresponding positions. Thus the adjusted reconstruction parameters may be adopted to reconstruct the three-dimensional blood vessel model using X-ray angiographic images. In some embodiments, the three-dimensional reconstruction adjustment unit 904 may output a calibrated three-dimensional model of a blood vessel.

For the specific implementation steps and methods of each unit of the device 900, reference may be made to corresponding steps and methods detailed in the foregoing method embodiments, and the description of which are omitted.

Figure 11:
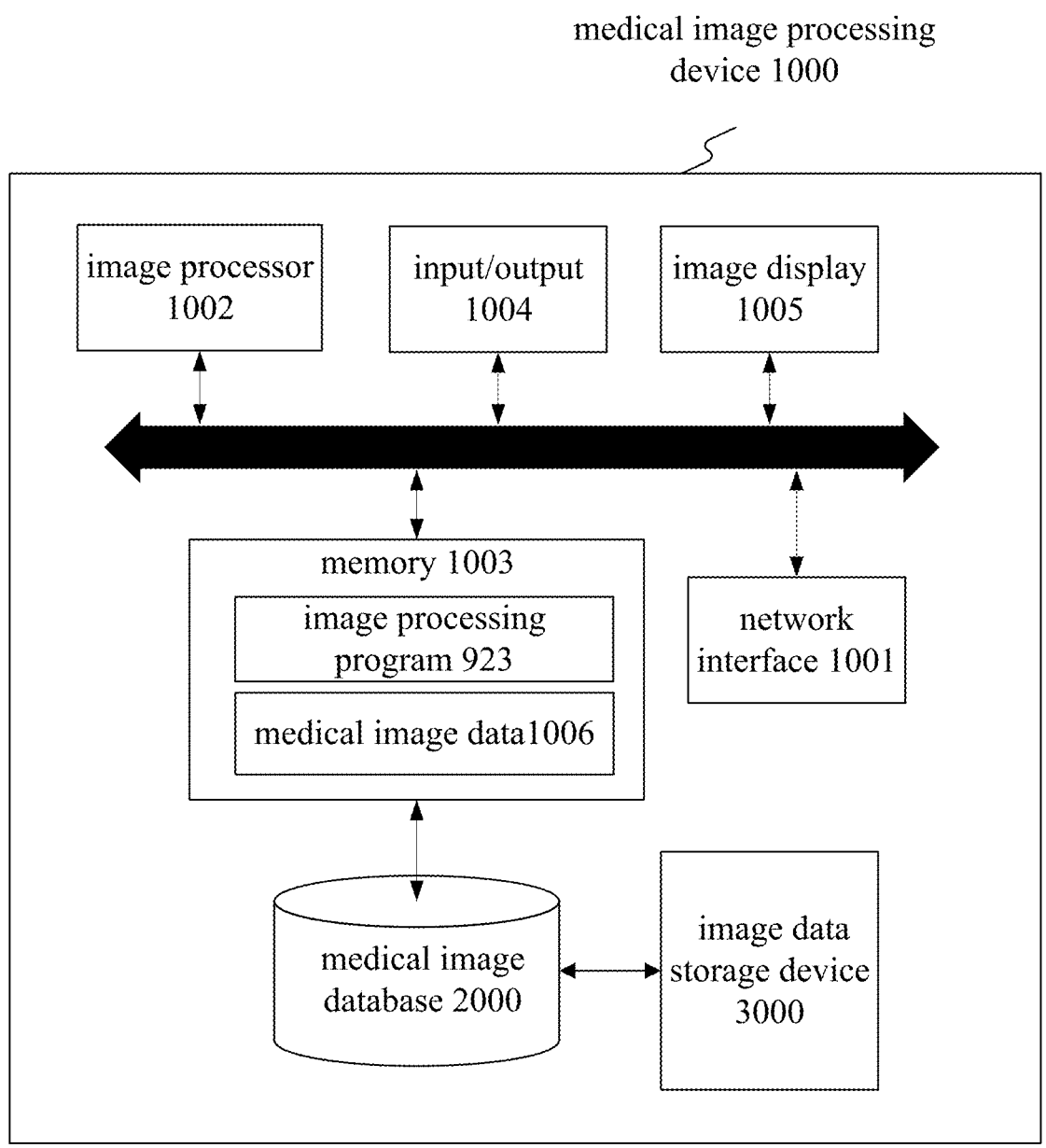
FIG. 11 illustrates a block diagram of a medical image processing device 1000 for performing three-dimensional blood vessel reconstruction using X-ray angiographic images.

FIG. 11 illustrates a block diagram of a medical image processing device 1000 for performing three-dimensional blood vessel reconstruction using X-ray angiographic images. The medical image processing device 1000 may include a network interface 1001 by which the device 1000 may be connected to a network (not shown) such as, but not limited to, a local area network in a hospital or the Internet. The network may connect the device 1000 with an external device such as an image acquisition device (not shown), a medical image database 2000, and an image data storage device 3000.

It is contemplated that the devices and methods disclosed in the embodiments may be implemented using a computer device. In some embodiments, the medical image processing device 1000 may be a dedicated smart device or a general-purpose smart device. For example, the medical image processing device 1000 may be a computer customized for image data acquisition and image data processing tasks, or a server placed in the cloud. For example, the device 1000 may be integrated into an image acquisition device. Optionally, the device may include or cooperate with a three-dimensional model reconstruction unit for generating a reconstructed three-dimensional model based on the two-dimensional images acquired by the image acquisition device.

The medical image processing device 1000 may include an image processor 1002 and a memory 1003, and may additionally include at least one of an input/output 1004 and an image display 1005.

The image processor 1002 may be a processing device including one or more general-purpose processing devices such as a microprocessor, a central processing unit (CPU), a graphics processing unit (GPU), and the like. More specifically, the image processor 1002 may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. The image processor 1002 may also be one or more dedicated processing devices such as application specific integrated circuits (ASICs), field programmable gate arrays (FPGAs), digital signal processors (DSPs), system-on-chip (SoCs), and the like. As would be appreciated by those skilled in the art, in some embodiments, the image processor 1002 may be a special-purpose processor, rather than a general-purpose processor. The image processor 1002 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The image processor 1002 may also include graphical processing units such as a GPU from the GeForce®, Quadro®, Tesla® family manufactured by Nvidia™, GMA, Iris™ family manufactured by Intel™, or the Radeon™ family manufactured by AMD™. The image processor 1002 may also include accelerated processing units such as the Desktop A-4 (6, 8) Series manufactured by AMD™, the Xeon Phi™ family manufactured by Intel™.

The disclosed embodiments are not limited to any type of processor(s) or processor circuits otherwise configured to meet the computing demands of identifying, analyzing, maintaining, generating, and/or providing large amounts of imaging data or manipulating such imaging data to calibrate a three-dimensional vessel model or to manipulate any other type of data consistent with the disclosed embodiments. In addition, the term "processor" or "image processor" may include more than one processor, for example, a multi-core design or a plurality of processors each having a multi-core design. The image processor 1002 can execute sequences of computer program instructions, stored in memory 1003, to perform various operations, processes, methods disclosed herein.

The image processor 1002 may be communicatively coupled to the memory 1003 and configured to execute computer-executable instructions stored therein. The memory 1003 may include a read only memory (ROM), a flash memory, random access memory (RAM), a dynamic random-access memory (DRAM) such as synchronous DRAM (SDRAM) or Rambus DRAM, a static memory (e.g., flash memory, static random-access memory), etc., on which computer executable instructions are stored in any format. In some embodiments, the memory 1003 may store computer-executable instructions of one or more image processing program(s) 923 and the data generated when the image processing program(s) are performed. The computer program instructions can be accessed by the image processor 1002, read from the ROM, or any other suitable memory location, and loaded in the RAM for execution by the image processor 1002, so as to implement each step of above methods. The image processor 1002 may also send/receive medical image data to/from storage 1003. For example, memory 1003 may store one or more software applications. Software applications stored in the memory 1003 may include, for example, an operating system (not shown) for common computer systems as well as for soft-controlled devices. Further, memory 1003 may store an entire software application or only a part of a software application (e.g. the image processing program (s) 923) to be executable by the image processor 1002. In some embodiments, the image processing program 923 may include the simulated optical path length determining unit 903 and the three-dimensional reconstruction adjustment unit 904 shown in FIG. 10 as software units, for implementing each step of the method or process of three-dimensional reconstruction using X-ray angiographic images consistent with the present disclosure. In some embodiments, the image processing program 923 may also include the three-dimensional model reconstructing unit 901 shown in FIG. 10 as a software unit. In addition, the memory 1003 may store data generated/cached when the computer program is executed, such as medical image data 1006, which includes medical images transmitted from an image acquisition device, the medical image database 2000, the image data storage device 3000, and the like. Such medical image data 1006 may include a received three-dimensional vessel model to be calibrated and the two-dimensional angiographic images corresponding thereto. In addition, the medical image data 1006 may also include any one of a calibrated three-dimensional vessel model, the difference on the optical path length, and the adjusted reconstruction parameters.

The image processor 1002 may execute an image processing program 923 to implement a method for three-dimensional vessel reconstruction using X-ray angiographic images. In some embodiments, when the image processing program 923 is executed, the image processor 1002 may associate the acquired reconstructed blood vessel three-dimensional model with the adjusted reconstruction parameters and the generated calibrated blood vessel three-dimensional model and store them in memory 1003. Alternatively, the image processor 1002 may associate the acquired reconstructed blood vessel three-dimensional model with the adjusted reconstruction parameters and the generated calibrated blood vessel three-dimensional model and send them to the medical image database 2000 via the network interface 1001.

It is contemplated that the device may include one or more processors and one or more memory devices. The processor(s) and storage device(s) may be configured in a centralized or distributed manner.

The device 1000 may include one or more digital and/or analog communication device (input/output 1004). For example, the input/output 1004 may include a keyboard and a mouse that allow the user to provide an input.

Device 1000 may be connected to the network through network interface 1001. The network interface 1001 may include a network adapter, a cable connector, a serial connector, a USB connector, a parallel connector, a high-speed data transmission adapter such as optical fiber, USB 3.0, lightning, a wireless network adapter such as a WiFi adapter, a telecommunication (3G, 4G/LTE, etc.) adapters. The network may provide the functionality of local area network (LAN), a wireless network, a cloud computing environment (e.g., software as a service, platform as a service, infrastructure as a service, etc.), a client-server, a wide area network (WAN), and the like.

The device 1000 may further include an image display 1005. In some embodiments, the image display 1005 may be any display device suitable for displaying a vascular angiographic image(s) and the three-dimensional reconstruction results. For example, the image display 1005 may be an LCD, CRT, or LED display.

Various operations or functions are described herein that may be implemented as software code or instructions or as software code or instructions. Such content may be directly executable source code or difference code ("incremental" or "block" code) ("object" or "executable" form). The software codes or instructions may be stored in a computer-readable storage medium and, when executed, may cause the machine to perform the described functions or operations and include any mechanism for storing information in a form accessible by the machine (e.g., computing devices, electronic systems, etc.), such as recordable or non-recordable media (e.g., read-only memory (ROM), random access memory (RAM), disk storage media, optical storage media, flash memory devices, etc.).

Although described using X-ray images, imaging modalities in the disclosed systems and methods may be alternatively or additionally applied to other imaging modalities where the pixel intensity varies with the distance traveled by imaging particles, such as CT, cone beam computed tomography (CBCT), Spiral CT, positron emission tomography (PET), single-photon emission computed tomography (SPECT), etc.

Following long-standing patent law convention, the terms "a", "an", and "the" refer to "one or more (at least one)" when used in this application, including the claims. Thus, for example, reference to "a unit" includes a plurality of such units, and so forth.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the term "and/or" when used in the context of a listing of entities, refers to the entities being present singly or in combination. Thus, for example, the phrase "A, B, C, and/or D" includes A, B, C, and D individually, but also includes any and all combinations and combinations of A, B, C, and D.

Another aspect of the disclosure is directed to a non-transitory computer-readable medium storing instructions which, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

It will be apparent to those skilled in the art that various modifications and variations can be made to the disclosed system and related methods. Other embodiments will be apparent to those skilled in the art from consideration of the specification and practice of the disclosed system and related methods.

It is intended that the specification and examples be considered as exemplary only, with a true scope being indicated by the following claims and their equivalents.

What is claimed is:

1. A computer-implemented method for performing three-dimensional blood vessel reconstruction using projection images of a patient, wherein the computer-implemented method comprises:
    receiving a first two-dimensional image of a blood vessel in a first projection direction and a three-dimensional model of the blood vessel;
    determining, by a processor, a first optical path length at a selected position of the blood vessel based on the first two-dimensional image;
    determining, by the processor, a second optical path length at the selected position of the blood vessel in the three-dimensional model; and
    adjusting the three-dimensional model of the blood vessel, based on a comparison of the first optical path length and the second optical path length.

2. The computer-implemented method according to claim 1, wherein determining the first optical path length further comprises:
    deriving from the first two-dimensional image an intensity value corresponding to the selected position of the blood vessel; and
    determining the first optical path length as linearly proportional to the intensity value.

3. The computer-implemented method according to claim 2, wherein deriving the intensity value further comprising:
    processing a pixel value of the first two-dimensional image corresponding to the selected position of the blood vessel.

4. The computer-implemented method according to claim 3, wherein deriving the intensity value further comprising:
    removing a background value from the pixel value of the first two-dimensional image before or after the processing.

5. The computer-implemented method according to claim 1, wherein determining the second optical path length further comprises:
    determining a size of the blood vessel in the three-dimensional model at the selected position in the first projection direction.

6. The computer-implemented method of claim 1, wherein determining the second optical path length further comprises:
    determining a diameter of a segment of the blood vessel based on a second two-dimensional image obtained by projecting the three-dimensional model in the first projection direction;
    determining an angle between the center line of the segment of the blood vessel and the first projection direction; and
    calculating the second optical path length within the segment of the blood vessel based on the diameter and the angle.

7. The computer-implemented method according to claim 1, wherein adjusting the three-dimensional model further comprises:
    determining a difference between the first optical path length and the second optical path length; and
    providing an indication when the difference is greater than a predetermined threshold.

8. The computer-implemented method according to claim 1, wherein adjusting the three-dimensional model further comprises:
    adjusting a size of the blood vessel at the selected position in the first projection direction in the three-dimensional model based on the comparison of the first optical path length and the second optical path length.

9. The computer-implemented method of claim 1, the method further comprising:
    reconstructing the three-dimensional model of the blood vessel from the projection images from multiple projection directions including the first two-dimensional image.

10. The computer-implemented method of claim 1, wherein the first two-dimensional image is an X-ray angiographic image of the patient.

11. A computer-implemented method for performing three-dimensional blood vessel reconstruction using projection images of a patient, wherein the computer-implemented method comprises:

receiving a first two-dimensional image of a blood vessel in a first projection direction and a three-dimensional model of the blood vessel;

determining, by a processor, optical path lengths at a plurality of positions of the blood vessel in the three-dimensional model in the first projection direction;

determining, by the processor, a second two-dimensional image based on the determined optical path lengths at the plurality of positions; and adjusting the three-dimensional model of the blood vessel, based on a comparison of the first two-dimensional image and the second two-dimensional image.

12. The computer-implemented method according to claim 11, wherein determining the second two-dimensional image further comprises:

determining intensity values of the second two-dimensional image as linearly proportional to the optical path lengths.

13. The computer-implemented method according to claim 11, wherein adjusting the three-dimensional model further comprising:

processing the first two-dimensional image; and comparing the processed first two-dimensional image with the second two-dimensional image.

14. The computer-implemented method according to claim 13, wherein adjusting the three-dimensional model further comprising:

determining a difference between the processed first two-dimensional and the second two-dimensional image; and adjusting the three-dimensional model when the difference is less than or equal to a predetermined threshold.

15. A device for performing three-dimensional blood vessel reconstruction using projection images of a patient, comprising:

an interface configured to receive a first two-dimensional image of a blood vessel in a first projection direction and a three-dimensional model of the blood vessel;

a processor, configured to:

determine a first optical path length at a selected position of the blood vessel based on the first two-dimensional image;

determine a second optical path length at the selected position of the blood vessel in the three-dimensional model; and adjust the three-dimensional model of the blood vessel, based on a comparison of the first optical path length and the second optical path length.

16. The device of claim 15, wherein to determine the first optical path length, the processor is further configured to:

derive from the first two-dimensional image an intensity value corresponding to the selected position of the blood vessel; and determine the first optical path length as linearly proportional to the intensity value.

17. The device of claim 16, wherein to derive the intensity value, the processor is further configured to:

process a pixel value of the first two-dimensional image corresponding to the selected position of the blood vessel.

18. The device of claim 15, wherein to determine the second optical path length, the processor is further configured to:

determine a size of the blood vessel in the three-dimensional model at the selected position in the first projection direction.

19. The device of claim 15, wherein to adjust the three-dimensional model, the processor is further configured to:

adjust a size of the blood vessel at the selected position in the first projection direction in the three-dimensional model based on the comparison of the first optical path length and the second optical path length.

20. The device of claim 15, wherein the three-dimensional model of the blood vessel is reconstructed from the projection images of the patient from multiple projection directions including the first two-dimensional image.

* * * * *